United States Patent [19]
Meguro

[11] Patent Number: 5,695,459
[45] Date of Patent: Dec. 9, 1997

[54] IONTOPHORESIS SYSTEM

[75] Inventor: Yasuo Meguro, Hino, Japan

[73] Assignee: Hisamitsu Pharmaceutical Co., Inc., Saga, Japan

[21] Appl. No.: 557,017

[22] PCT Filed: Jun. 8, 1994

[86] PCT No.: PCT/JP94/00932

§ 371 Date: Dec. 6, 1995

§ 102(e) Date: Dec. 6, 1995

[87] PCT Pub. No.: WO94/28967

PCT Pub. Date: Dec. 22, 1994

[30] Foreign Application Priority Data

Jun. 8, 1993 [JP] Japan .................. 5-163299

[51] Int. Cl.[6] .................................................. A61N 1/30
[52] U.S. Cl. .................................... 604/20; 607/72
[58] Field of Search ........................... 604/20; 607/1, 607/72, 74, 115, 120; 606/32, 34

[56] References Cited

U.S. PATENT DOCUMENTS 4,942,883  7/1990  Newman .................. 128/798
5,088,977  2/1992  Sibalis ..................... 604/20
5,254,081  10/1993 Maurer et al. ............. 604/20
5,380,272  1/1995  Gross ...................... 604/20

FOREIGN PATENT DOCUMENTS

61680A3  12/1991  European Pat. Off. .
28125A1  7/1991   Germany .
345272   2/1991   Japan .
224770   8/1992   Japan .

Primary Examiner—Mark Bockelman
Assistant Examiner—Ellen S. Too
Attorney, Agent, or Firm—Christie, Parker & Hale, LLP

[57] ABSTRACT

The present invention relates to an iontophoresis system. A power supply circuit for applying pulsating voltages to iontophoretic elements includes an element selector and a potential difference generating unit. The element selector selects a combination of iontophoretic elements according to given timing. The potential difference generating unit generates a potential difference between a selected combination of iontophoretic elements by applying pulsating voltages to the iontophoretic elements at different time periods. When the system is in operation, the iontophoretic elements will not be kept at a certain potential and undesirable electrode reactions can be prevented from occurring at each iontophoretic element.

5 Claims, 4 Drawing Sheets

IONTOPHORESIS SYSTEM

TECHNICAL FIELD

The present invention relates to an iontophoresis system for percutaneously administering a medicine by means of an electric current.

BACKGROUND ART

An iontophoresis system comprises a pair of iontophoretic elements (hereinafter elements) each containing, for example, an ionic drug or medicine, and a power source for applying pulsating voltages to the elements. In the system, the elements are placed on the skin, and then pulsating voltages are applied to the elements. An electrically-closed circuit is thus formed via the skin, whereby a medicine is introduced into a human body. The conductivity of the thus formed electrically closed circuit is dependent greatly on the states of the elements contacting the skin. The electrodes in the elements, which are connected to the power source, are deposited in the same environment as a fluid containing an ionic drug or medicine. Besides, when the system is in operation, voltages that are pulsating in one direction are applied intermittently to the electrodes. Therefore, the electrodes may undergo chemical changes, or electrolysis or adhesion of electrically insulating materials may occur at the surfaces of the electrodes.

The conductivity of the electrically closed circuit therefore deteriorates with the variations of the states of the electrodes in the elements in the system. The persistence of the efficacy of the medication is therefore impaired.

DISCLOSURE OF THE INVENTION

The objects of the present invention are to provide an iontophoresis system in which electrodes in the elements are not susceptible to the influence of electrode reactions such as chemical changes and electrolysis, and to improve the persistence of efficacy of medication.

According to the present invention, an iontophoresis system comprises at least three elements any or all of which contain a medicine, and a power supply means for applying pulsating voltages to any pair of elements so as to generate a potential difference between the pair of elements. The power supply means includes a device selecting means for selecting a combination of elements from among the at least three elements according to a given timing, and a potential difference generating means for generating a potential difference between a selected combination of elements by applying pulsating voltages to the elements over different time periods.

In a preferred embodiment of the present invention, the potential difference generating means preferably generates potential differences between selected combinations of elements by applying a voltage, which is opposite in polarity to the polarity of a voltage applied to at least one of the elements which was selected previously, to the element. The device selecting means preferably selects combinations of elements, in a given order, cyclically.

In another preferred embodiment of the present invention, a selected combination of elements is a pair of elements. The potential difference generating means preferably retains any element other than the selected elements in an electrically neutral state.

In yet another preferred embodiment of the present invention, the at least three elements are in one package.

According to the foregoing embodiments of the present invention, any combination of elements is selected according to a given timing. A potential difference is generated between combinations of elements by applying pulsating voltages to the elements at different time periods. The phase of a pulsating voltage to be applied to each element is inverted according to the given timing and the electrodes in the elements are renewed. Thus the aforesaid problem concerning electrode reactions is solved.

When a combination of elements is a pair of elements, the phase of a pulsating voltage to be applied to each element is inverted efficiently and effectively.

Moreover, since any element other than the selected elements is retained in an electrically neutral state, the power consumption of a power source in the system can be minimized.

According to the present invention, the electrodes in the elements can be refreshed and the occurrence of electrode reactions in the electrodes can be avoided or suppressed. This system thus provides stable percutaneous medication for a prolonged period of time.

BRIEF DESCRIPTION OF THE DRAWINGS

The aforesaid object and other objects, features, and advantages of the present invention will be described in detail in conjunction with the appended drawings.

BEST MODE FOR CARRYING OUT THE INVENTION

Figure 1:
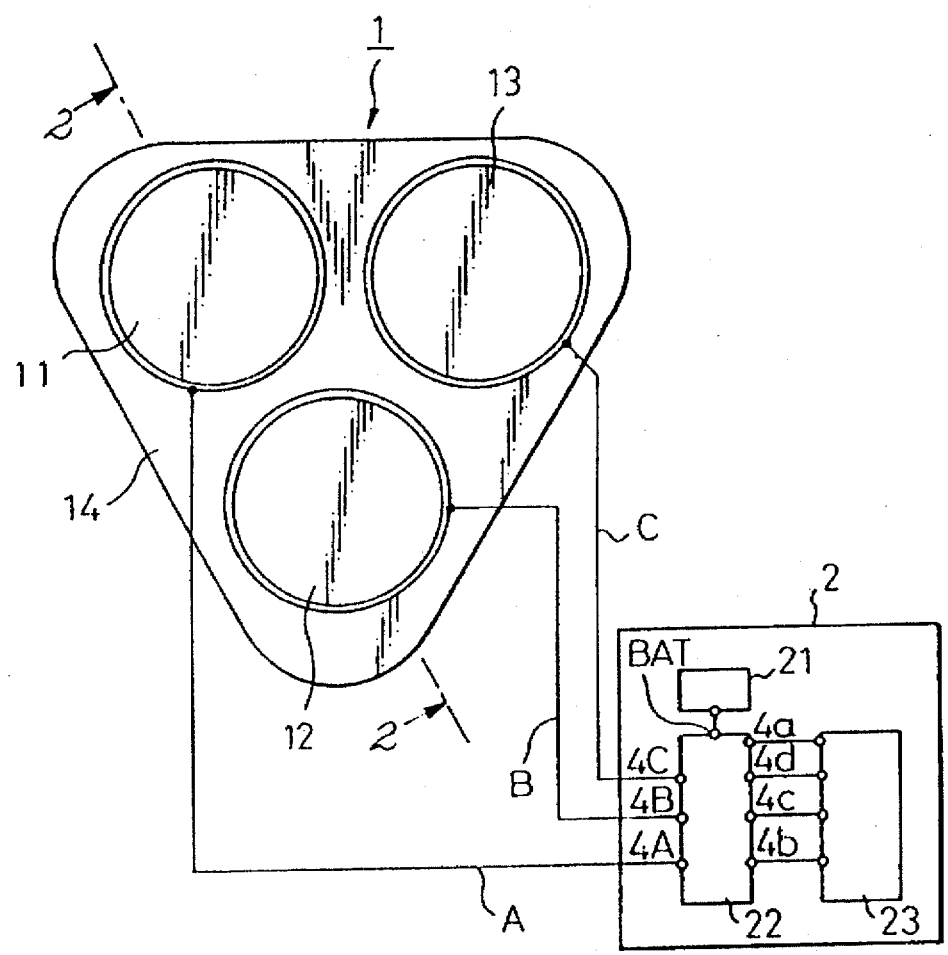
FIG. 1 is a bottom view showing a first embodiment of an iontophoresis system in accordance with the present invention.

To begin with, the configuration of the first embodiment of an iontophoresis system in accordance with the present invention will be described in conjunction with FIGS. 1 and 2.

An iontophoresis system of this embodiment comprises an iontophoretic element unit 1 (hereinafter an element unit) to be placed on the skin of a living body, and a power supply unit 2 for supplying pulsating voltages to the unit 1. The element unit 1 is composed of elements 11, 12, and 13 to be connected to the power supply unit 2 by way of power lines A, B, and C, and an adherent section 14 for retaining the element unit 1 on the skin of a living body by means of adhesion. The elements 11, 12, and 13 and the adherent section 14 are covered with a package 15. The power supply unit 2 includes a power source 21 that is a battery or any other appropriate source, a pulsating voltage producing circuit 22 for producing pulsating voltage outputs, and a control unit 23 for controlling the pulsating voltage producing circuit 22.

In this embodiment, the element unit 1 and power supply unit 2 are separated from each other. Alternatively, the element unit 1 and power supply unit 2 may be integrated into one unit. In this case, the power supply unit 2 must be designed compactly using a button cell and an integrated circuit.

In this embodiment, the elements have the same shape. Each or any of the elements contains a drug or medicine. The element 11 or 12 is, as shown in FIG. 2, composed of an electrode 111 or 112 connected to the power supply unit 2 and an interfacing member 121 or 122 containing a drug or medicine.

The electrodes 111 and 112 are made of a conductive material, preferably, an inactive raw material such as Ag—AgCl. The conductive material is not limited to Ag—AgCl. The interfacing members 121 and 122 are formed with a porous member or a conductive gel. A preferable example of the porous member is a film member having water absorbency or water permeability, for example, a laminated membrane filter (Biodyne A (trade mark)), a nonwoven fabric, a multilayer member made of water permeable fibers; such as, a porous film, (for example, a wafer) starch composed of water-soluble high molecular weight materials and capable of holding, adhering, or encapsulating a given drug or medicine, or a water-absorbent (or –soluble) film such as a PVP film.

The degree of the water solubility of a porous member and the content of a drug or medicine in the porous member are specified or adjusted appropriately according to the purpose of the iontophoresis system.

Figure 3:
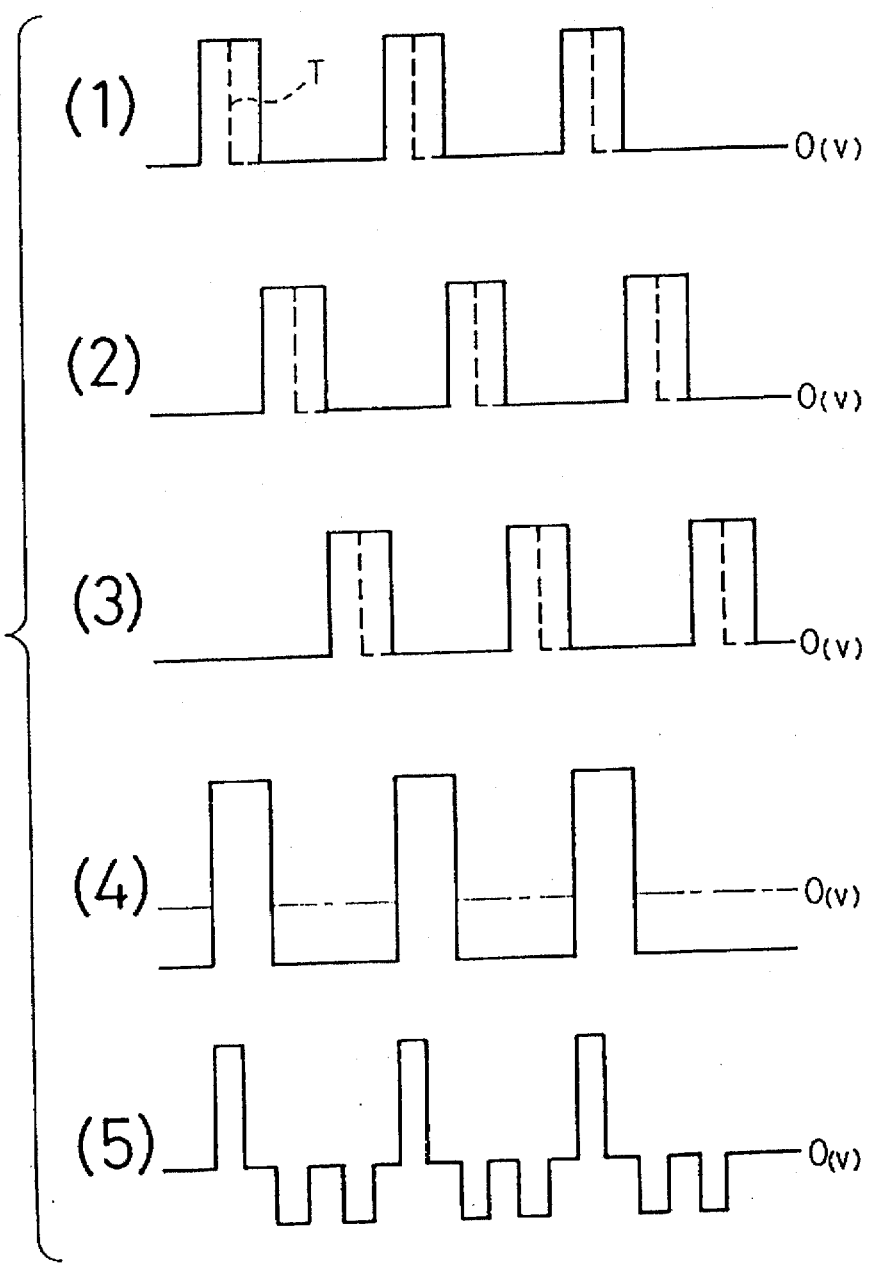
FIGS. 3 lines 1 to 35 are timing charts showing voltages applied to respective components of the system shown in FIG. 1, wherein (1) shows a pulsating voltage supplied from a pulsating voltage producing circuit to elements 11 and 12, (2) shows a pulsating voltage supplied from the pulsating voltage producing circuit to elements 12 and 13, (3) shows a pulsating voltage supplied from the pulsating voltage producing circuit to the elements 13 and 11, (4) shows voltage fluctuations occurring at the elements 11 and 12, and (5) shows voltage fluctuations occurring at the elements 11 and 12 when pulsating voltages are applied according to another method.

Next, the operations of the iontophoresis system will be described in conjunction with FIG. 3.

After the element unit 1 is placed on an object region for medication on the skin, the power supply unit 2 is energized. The power supply unit 2 applies pulsating voltages, which can be set to any value ranging from several volts to several tens of volts, to the elements 11 and 12 by way of the lead wires A and B respectively. At this time, the power supply unit 2 applies the pulsating voltages so as to cause the potential at the element 11 to go high (positive) and the potential at the element 12 to go low (negative), and thus generates a potential difference between the elements 11 and 12. After applying the pulsating voltages to the elements 11 and 12, the power supply unit 2 applies pulsating voltages to the elements 12 and 13 by way of the lead wires B and C according to given timing (See FIG. 3(2)). At this time, the power supply unit 2 applies the pulsating voltages so as to cause the potential at the element 12 to go high (positive) and the potential at the element 13 to go low (negative), and thus generates a potential difference between the elements 12 and 13. After applying the pulsating voltages to the elements 12 and 13, the power supply unit 2 applies pulsating voltages to the elements 13 and 11 by way of the lead wires C and A synchronously with a given voltage (See FIG. 3(3)). At this time, the power supply unit 2 applies the pulsating voltages so as to cause the potential at the element 13 to go high (positive) and the potential at the element 11 to go low (negative), and thus generates a potential difference between the elements 13 and 11.

Figure 5:
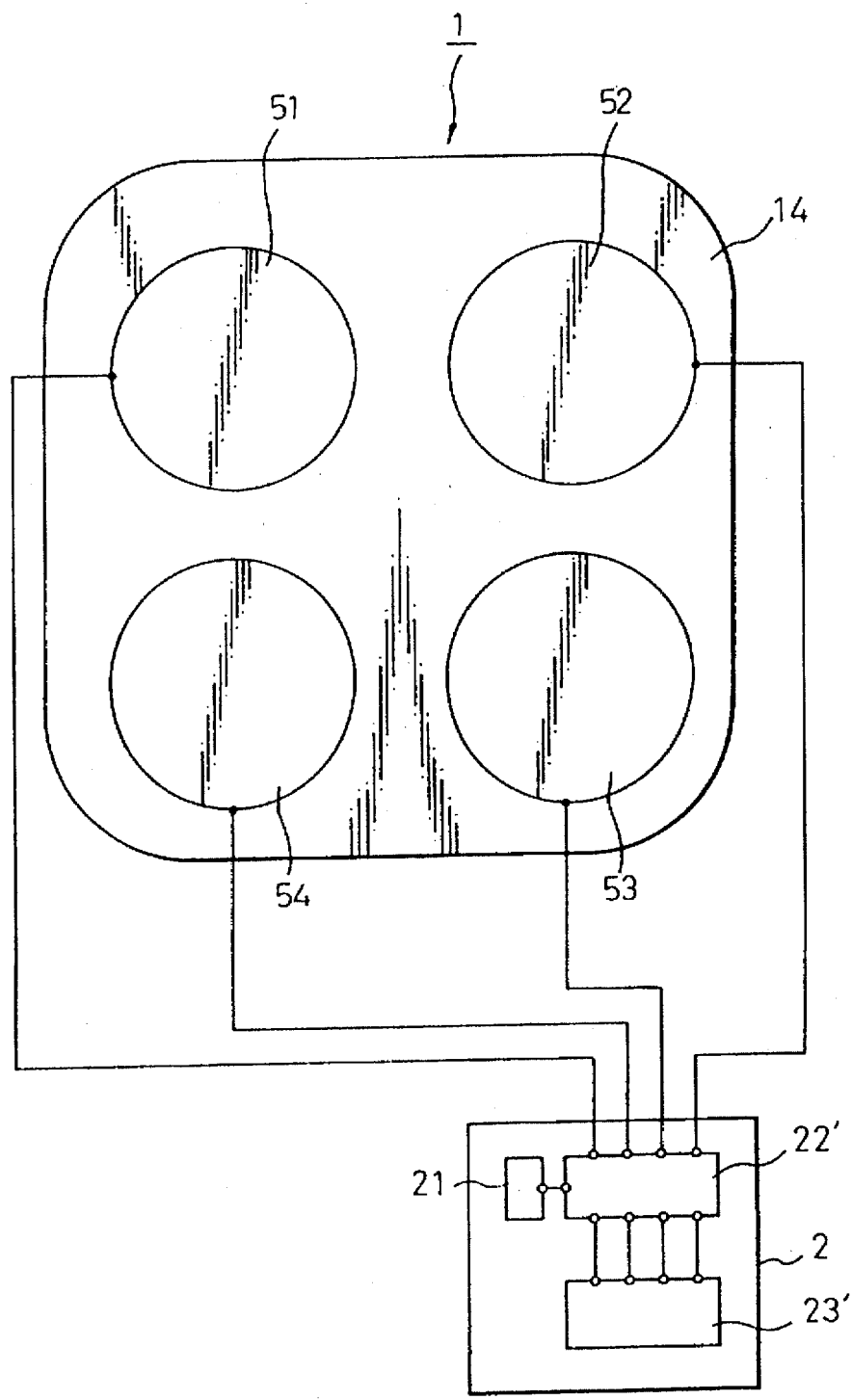
FIG. 5 is a bottom view showing a second embodiment of an iontophoresis system in accordance with the present invention.

Thereafter, the power supply unit 2 repeatedly executes the foregoing sequence of pulsating voltage application by inverting the phase of a pulsating voltage to be applied to each element. FIG. 3(4) shows voltage fluctuations occurring at the elements 11 and 12 during the sequence. The potential generating means generates positive pulses each having a maximum duty cycle, i.e., time duration of the positive pulse as a ratio to the total time period between leading edges of the positive pulses, equal to 1/n, wherein n is equal to the number of iontophoretic elements. In the described embodiment, the maximum duty ratio of voltage pulses applied to any one pair of elements selected from the three elements is 33%. In the embodiment of FIG. 5, yet to be described, with four elements, the duty cycle is 25%. Since the phase of a pulsating voltage to be applied to each element is inverted during each period of application, electrode reactions causing the conductivity of each element to deteriorate can be avoided and the occurrence of polarization charge causing a burn can be prevented.

Next, the configuration of the power supply unit 2 producing the aforesaid sequence of pulsating voltages will be described in conjunction with FIGS. 1 to 4.

Figure 2:
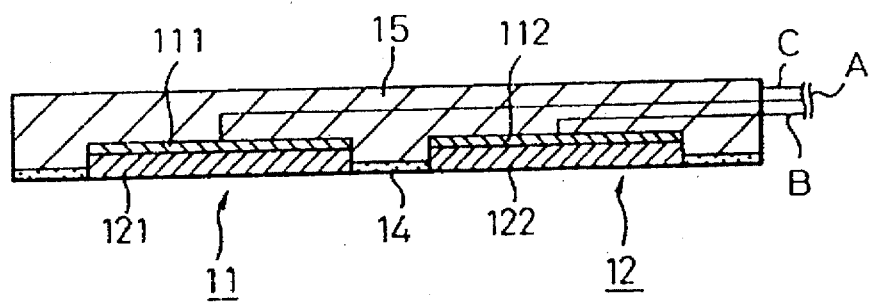
FIG. 2 shows an X-X' section of the system shown in FIG. 1.

The power supply unit 2 is, as shown in FIG. 1, composed of the power source 21 such as a battery, the control unit 23, and the pulsating voltage producing circuit 22 for producing pulsating voltages in response to a signal sent from the control unit 23.

The control unit 23 can be realized with one or a plurality of one-chip microcomputers each comprising, for example, a CPU, a clock generator, a voltage divider for producing a pulsating signal of a given frequency on the basis of a clock generated by the clock generator, a memory means for storing a program for executing the sequence of pulsating voltage application and coefficients to be specified in the program, and an interface means for providing an interface with the pulsating voltage producing circuit. The control unit 23 feeds a first pulsating signal of a given frequency to an input port 4a of the pulsating voltage producing circuit, and a second pulsating signal, which lags behind the first pulsating signal by a given time, sequentially to input ports 4b to 4d. The first pulsating signal is used to cause the pulsating voltage producing circuit 22 to produce a high voltage. The second pulsating signal is used as a select signal enabling selective application of a pulsating voltage to the elements.

The frequency of the first pulsating signal fed to the input port 4a ranges, for example, from 1 kHz to 10 MHz. The frequency of the second pulsating signal fed to each of the input ports 4b to 4d is, for example, several tens of kHz. These pulsating signals are produced by the voltage divider in the control circuit 23. Alternatively, an oscillator such as a multivibrator may be used for producing the pulsating signals. A pulsating signal having a frequency of 40 kHz and a duty ratio of about 30% is supplied, as an output resulting from phase inversion, to each of the input ports 4b to 4d.

Figure 4:
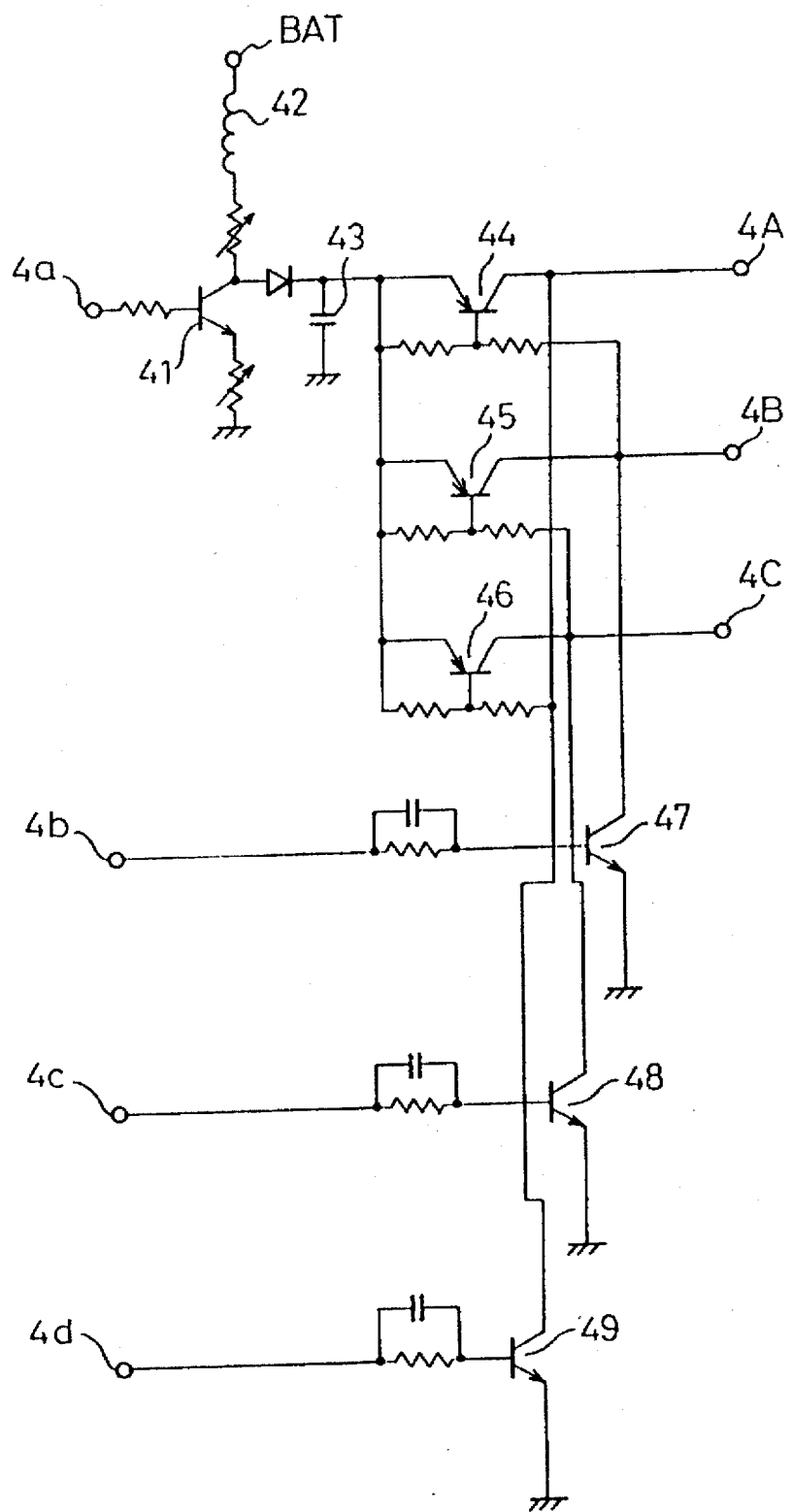
FIG. 4 is a circuit diagram showing an example of a pulsating voltage producing circuit in a power supply unit shown in FIG. 1.

The pulsating voltage producing circuit 22 is, as shown in FIG. 4, composed of a plurality of switching transistors 41 and 44 to 49, an inductor 42, and a capacitor 43. The power source 21 such as a battery shown in FIG. 1 is connected to a terminal BAT of the pulsating voltage producing circuit 22. The elements 11, 12, and 13 are connected to the output ports 4A to 4C by way of the lead wires A to C.

The operations of the pulsating voltage producing circuit 22 will be described below.

When a first pulsating signal is fed to the input port 4a, the transistor 41 is turned on or off synchronously with the pulsating signal. When the transistor 41 is turned on, an excitation current flows into the inductor 42. When the transistor 41 is turned off, a boosted pulse whose level is several times to several tens of times larger than the supply voltage is generated due to the energy released by the inductor 42. The boosted pulse is stored in the capacitor 43 via a diode, and then used as pulsating power to be applied to each element.

When a second pulsating signal, serving as a select signal, is fed from the control unit to the input port 4b, the transistor 47 is turned on at the leading edge of the select signal. The transistor 44 is turned on synchronously with the transistor 47. The voltage stored in the capacitor 43 is then delivered to each of the output ports 4A and 4B. Thereafter, when the select signal fed to the input port 4b is driven low, the transistors 44 and 47 are turned off. Application of voltages to the elements 11 and 12 via the output ports 4A and 4B is then terminated. Thus, pulsating voltages corresponding to the select signal are applied to the elements 11 and 12.

A given time later, when another select signal is fed from the control unit 23 to the input port 4c, the transistors 45 and 48 are activated. A pulsating voltage causing the potential at the output port 4B to go high is delivered to each of the output ports 4B and 4C. Output pulsating voltages are then applied to the elements 12 and 13.

A given time later, when yet another select signal is fed from the control unit 23 to the input port 4d, the transistors 46 and 49 are activated. A pulsating voltage causing the potential at the output port 4C to go high is delivered to each of the output ports 4C and 4A. Output pulsating voltages are then applied to the elements 13 and 11.

Note that since the pulsating voltage producing circuit 22 has the aforesaid circuitry, the potentials at the output ports are inverted with every input of a select signal from the control unit 23.

As mentioned above, select signals that lag behind previous signals by given times are consecutively applied to the input ports 4b, 4c, and 4d. A pulsating voltage, whose phase is inverted, is fed sequentially to any pair of the output ports 4A, 4B, and 4C. Consequently, a pulsating voltage whose phase is inverted is applied sequentially to each pair of the elements 11, 12, and 13.

The second embodiment of an iontophoresis system in accordance with the present invention will be described in conjunction with FIG. 5.

An iontophoresis system shown in FIG. 5 has four elements. The configuration and inner structure are identical to those shown in FIGS. 1 and 2. The description of the configuration and inner structure will therefore be omitted. Any medicine can be contained in each of the elements 51, 52, 53, and 54.

The application of pulsating voltages in this embodiment will be described. First, a pair of the elements 51 and 52 is selected with a first select signal fed from a control unit 23' in the power supply unit 2. A pulsating voltage producing circuit 22' applies pulsating voltages to the elements 51 and 52, thus causing the potential at the element 51 to go high (positive) and the potential at the element 51 to go low (negative). With another select signal, a pair of the elements 53 and 54 is selected. Pulsating voltages are then applied to the elements 53 and 54, thus causing the potential at the element 53 to go high and the potential at the element 54 to go low. A pair of the elements 54 and 51 is selected with the next select signal. This causes the potential at the element 54 to go high and the potential at the element 51 to go low. A pair of the elements 52 and 53 is then selected with another select signal. This causes the potential at the element 52 to go high and the potential at the element 53 to go low. By executing the foregoing sequence repeatedly, a pulsating voltage is applied to an element, to which a previous pulsating voltage is applied via an output port whose potential is driven high, via the output port whose potential is driven low. Through the applications of pulsating voltages, the elements are not kept at either a high or a low potential. Electrode reactions causing conductivity to deteriorate can be prevented from occurring at the electrode in each element.

According to the present invention, the number of elements and the way of combining the elements are not limited to those in the aforesaid embodiments. Alternatively, five or more elements may be employed, and a plurality of elements may be paired with one element for the application of pulsating voltages. The configuration required for this alternative will be apparent, from the embodiments, to a person with an ordinary skill in the art. When the number of elements is increased, the numbers of input ports, output ports, and transistors shown in FIG. 4 should be increased accordingly. When a plurality of elements are paired with one element for application of pulsating voltages, a known diode matrix circuit or the like is used to select any of the transistors associated with the input ports and output ports shown in FIG. 4.

The order of applying pulsating voltages to elements, application times, timing, and combinations of elements can be changed by modifying a program written in a microcomputer employed in the aforesaid embodiments. For example, a pulse duration of a pulsating voltage applied to each element may be shortened as indicated with dashed lines T in FIGS. 3(1) to 3(3) and as shown in FIG. 3(5), and then a period between pulses may be regarded as a quiescent period. Owing to the definition of the quiescent period, the power consumption of a power supply unit can be minimized. This results in a compact system.

In the aforesaid embodiments, a plurality of elements are stowed in an element unit. Alternatively, the elements may be formed as stand-alone devices.

Finally, examples of drugs and medicines usable for an iontophoresis system in accordance with the present invention will be listed below.

Local anesthetic (lidocaine hydrochloride, tetracaine hydrochloride, procaine hydrochloride, dibucaine hydrochloride, oxyprocaine hydrochloride, bupivacaine hydrochloride, mepivacaine hydrochloride, etc.)

Antiallergic agent or antitussant and expectorant (sodium cromoglycate, ketotifen fumarate, azelastine hydrochloride, amlexanox, terfenadine, emedastine, fumarate, tranilast, codeine phosphate, dihydrocodeine phosphate, eprazinone hydrochloride, tipepidine hybenzate, etc.)

Bronchial dilator (theophylline, pirbuterol hydrochloride, terbutaline sulfate, hexoprenaline sulfate, salbutanol sulfate, tulobuterol hydrochloride, procaterol hydrochloride, mabuterol hydrochloride, formoterol fumarate, etc.)

Analgesic (morphine hydrochloride, hydromorphone hydrochloride, buprenorphine hydrochloride, bupranolol hydrochloride, pentazocine, butorphanol tartrate, eptazocine hydrobromide, nalbuphine hydrochloride, etc.)

Cardiac (dopamine hydrochloride, dobutamine hydrochloride, amrinone, etc.)

Tranquilizer (chlorpromazine hydrochloride, etizolam, amitriptyline hydrochloride, clocapramine dihydrochloride, haloperidol, mosapramine hydrochloride, perphenazine, etc.)

Antibiotic (penicillin antibiotics such as cloxacillin sodium, benzylpenicillin potassium, ticarcillin sodium, ampicillin sodium, and piperacillin sodium; cefm antibiotics such as cefoxitin sodium, cefodizime sodium, cefotaxime sodium, cefotetan, cefoperazone sodium, cefsulodin sodium, ceftazidime, cefmetazole sodium, and cefpirome sodium; amino sugar antibiotics such as gentamicin sodium, sisomicin sodium, dibekacin sodium, netilmicin sodium, amikacin sodium, and ribostamycin sodium; other antibiotics such as lincomycin, erythromycin, josamycin, chloramphenicol, and tetracycline)

Antimelanoma agent (mitomycin C, etoposide, procarbazine hydrochloride, tamoxifen citrate, fluorouracil, UFT, tegafur, carmofur, methotrexate, carboquone, bleomycin hydrochloride, peplomycin sulfate, epirubicin hydrochloride, pirarubicin hydrochloride, neocarzinostatin, lentinan, picibanil, sizofilan, cisplatin, carboplatin, adriamycin, vincristine sulfate, etc.)

Circulatory medicine (nicametate citrate, alprostadil, argatroban, citicoline, nizofenone fumarate, D-mannitol, nicorandil, diltriazem hydrochloride, etc.)

Gout treatment agent (benzbromarone, allopurinol, colchicine, etc.)

High lipemia agent (simvastatin, nicomol, pravastatin sodium, etc.)

Antihistamine (diphenhydramine hydrochloride, promethazine hydrochloride, chlorpheniramine maleate, mequitazine, clemastine fumarate, etc.)

Sleep abirritant or antianxiety agent (flunitrazepam, midazolam, secobarbital sodium, amobarbital sodium, phenytoin sodium, etc.)

Analgesic or antiphlogistic (ketoprofen, flurbiprofen axetil, indometacin, loxoprofen sodium, diclofenac sodium, piroxicam, tenidap, flurbirpfen, tenoxicam, etc.)

Anti-dizziness agent (difenidol hydrochloride, thiethylperazine maleate, betahistine mesylate, etc.)

Anticonvulsant (scopolamine buthylbromide, atropine sulfate, eperisone hydrochloride, tizanidine hydrochloride, etc.)

Arrhythmia agent (arotinolol hydrochloride, propranolol hydrochloride, atenolol, quinidine sulfate, indenolol hydrochloride, bucumolol hydrochloride, etc.)

Antihypertensive agent (clonidine hydrochloride, bethanidine sulfate, benazepril hydrochloride, cilazapril, captopril, celiprolol hydrochloride, tilisolol hydrochloride, terazosinn hydrochloride, bunnazosin hydrochloride, carvedilol, etc.)

Cortical hormone (hydrocortisone sodium phosphate, dexamethasone palmitate, dexamethasone sodium phosphate, betamethasone sodium phosphate, methylprednisolone succinate, etc.)

Peptide, polypeptide, and other drugs include luteinizing hormone-releasing hormone (LH-RH), enkephalin, endorphin, interferon, insulin, calcitonin, thyrotropin releasing hormone (TRH), oxytocin, lypressin, vasopressin, glucagon, pituitary hormone (human growth hormone (HGH), human menopausal gonadotrophin (HMG), human chorionic gonadotrophin (HCG), desmopressin acetate), follicile stimulating hormone, growth hormone releasing factor, adrenocorticotropic hormone (ACTH), parathyroid hormone (PTH), secretin, angiotensin, beta-endorphin, somatostatin, gastrin, neurotensin, atrial natriuretic peptide (ANP), bradykinin, substance P, dynorphin, thyroid-stimulating hormone (TSH), prolactin, interleukin, granulocyte colony-stimulating factor (G-CSF), glutathione peroxidase, superoxide dismutase (SOD), desmopressin, somatomedin, melanocyte-stimulating hormone (MSH), muramyl dipeptide, bombesin, vasoactive intestinal polypeptide, cholecystokinin-8, calcitonin gene relating peptide (CGRP), endothelin, and nicotine.

These agents are mixed with various matrix components available in pharmaceutics and can be used in various types of forms such as salve, gel, cream, solution, suspension, film, or the like.

I claim:

1. An iontophoresis system having at least three iontophoretic elements, any or all of which contains a medicine, and a power supply means connected to the elements for applying pulsating voltages to the elements so as to generate a potential difference between the elements, wherein:

said power supply means includes an element selecting means for cyclically selecting a pair of iontophoretic elements in a given order from among said at least three iontophoretic elements, and a potential difference generating means for generating a potential difference between said selected pairs of iontophoretic elements by applying pulsating voltages to the elements at different time instants;

wherein said potential difference generating means retains any iontophoretic element other than the selected iontophoretic elements in an electrically neutral state;

wherein said potential difference generating means generates a potential difference by applying a voltage to one of the iontophoretic elements of one of said selected pairs of iontophoretic elements such that said voltage pulsates in a direction opposite to a direction of a voltage previously applied to said one of the iontophoretic elements of a previously selected pair; and wherein said potential difference generating means generates potential differences so that each of any one pair of iontophoretic elements selected from among the at least three elements exhibits a voltage of the same polarity, and so that the polarity of each of the elements is periodically changed to the three states of positive polarity, negative polarity and electrically neutral.

2. The system according to claim 1, wherein said at least three iontophoretic elements are stowed in one package.

3. The iontophoresis system of claim 1 wherein a duty ratio of voltage pulses applied to any one pair of elements selected from among the at least three electrodes corresponds to an inverse number or less of the number of elements.

4. The iontophoresis system of claim 1 wherein the potential generating means generates positive pulses having a maximum duty cycle equal to 1/n, wherein n is equal to the number of iontophoretic elements.

5. An iontophoresis system having at least three iontophoretic elements, any or all of which contains a medicine, and a power supply means connected to the elements for applying pulsating voltages to the elements so as to generate a potential difference between the elements wherein:

said power supply means includes an element selecting means for cyclically selecting pairs of iontophoretic elements in a given order from among said at least three iontophoretic elements, and a potential difference generating means for generating a potential difference between said iontophoretic elements of said selected pairs by applying a positive pulse to one iontophoretic element and a negative pulse to the other iontophoretic element of said selected pair and retaining any iontophoretic elements other than the selected pair in an electrically neutral state, wherein said potential difference generating means generates said potential difference so that each of the iontophoretic elements of a selected pair always receives the same polarity pulse when said pair is selected by the element selecting means, each of the iontophoretic elements receiving a periodic waveform comprising a positive pulse, a negative pulse and electrically neutral state.

* * * * *

UNITED STATES PATENT AND TRADEMARK OFFICE
CERTIFICATE OF CORRECTION

PATENT NO.   : 5,695,459
DATED        : December 9, 1997
INVENTOR(S)  : Yasuo Meguro It is certified that error appears in the above-indentified patent and that said Letters Patent is hereby corrected as shown below:

Column 1, line 41, after "iontophoresis" delete "5".
Column 2, line 33, replace "FIGS. 3 lines 1 to 35" with
    -- FIG. 3 (1) to (5) --.

Signed and Sealed this

First Day of December, 1998

Attest:

BRUCE LEHMAN

Attesting Officer      Commissioner of Patents and Trademarks